US00PP15373P2

(12) United States Plant Patent
Westhoff

(10) Patent No.: US PP15,373 P2
(45) Date of Patent: Nov. 23, 2004

(54) ***PETUNIA* PLANT NAMED 'WESPECAROSE'**

(50) Latin Name: *Petunia×hybrida*
Varietal Denomination: Wespecarose

(75) Inventor: Heinrich Westhoff, Südlohn (DE)

(73) Assignee: Josef & Heinrich Westhoff Gartenbau-Spezialkulturen, Sudlohn-Oeding (DE)

( * ) Notice: Subject to any disclaimer, the term of this patent is extended or adjusted under 35 U.S.C. 154(b) by 0 days.

(21) Appl. No.: 10/759,728

(22) Filed: Jan. 16, 2004

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—Michelle Kizilkaya
(74) *Attorney, Agent, or Firm*—C. A Whealy

(57) ABSTRACT

A new and distinct cultivar of *Petunia* plant named 'Wespecarose', characterized by its cascading, roughly spherical growth habit; freely branching plant habit; freely flowering habit; single pastel pink-colored flowers with dark purple-colored venation; and light violet-colored anthers.

1 Drawing Sheet

Botanical classification/cultivar designation: *Petunia×hybrida* cultivar Wespecarose.

BACKGROUND OF THE INVENTION

The present Invention relates to a new and distinct cultivar of *Petunia* plant, botanically known as *Petunia×hybrida*, and hereinafter referred to by the name 'Wespecarose'.

The new *Petunia* is a product of a planned breeding program conducted by the Inventor in Südlohn-Oeding, Germany. The new *Petunia* originated from a cross-pollination made by the Inventor of a proprietary *Petunia* seedling selection, not patented, as the female, or seed parent, identified as code number 98K6384-340 with a proprietary *Petunia* seedling selection, not patented, as the male, or pollen, parent, identified as code number 98P037. The new *Petunia* was selected by the Inventor in 2000 in a controlled environment in Südlohn-Oeding, Germany.

Asexual reproduction of the new cultivar by terminal cuttings taken in Südlohn-Oeding, Germany since 2001, has shown that the unique features of this new *Petunia* are stable and reproduced true to type in successive generations.

SUMMARY OF THE INVENTION

Plants of the cultivar Wespecarose have not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Wespecarose'. These characteristics in combination distinguish 'Wespecarose' as a new and distinct *Petunia* cultivar:

1. Cascading and roughly spherical growth habit.
2. Freely branching plant habit.
3. Freely flowering habit.
4. Single pastel pink-colored flowers with purple-colored venation.
5. Light violet-colored anthers.

Plants of the new *Petunia* are more freely branching, have larger flowers and have flowers lighter pink in color than plants of the female parent. Plants of the new *Petunia* have a more trailing plant habit, have smaller flowers and have flowers are deeper pink in color than plants of the male parent.

Plants of the cultivar Wespecarose can be compared to plants of the *Petunia* cultivar Wespemab, disclosed in U.S. Plant Pat. No. 14,165. However in side-by-side comparisons conducted in Südlohn-Oeding, Germany, plants of the new *Petunia* and the cultivar Wespemab, differed in the following characteristics:

1. Plants of the new *Petunia* produced main branches that are longer than main branches of the cultivar Wespemab.
2. Plants of the new *Petunia* had longer internodes than plants of the cultivar Wespemab.
3. Plants of the new *Petunia* had larger leaves than plants of the cultivar Wespemab.
4. Plants of the new *Petunia* had larger flowers than plants of the cultivar Wespemab.
5. Flowers of the new *Petunia* had less pronounced venation than flowers of the cultivar Wespemab.
6. Flower color of the new *Petunia* was different than flower color of the cultivar Wespemab.

Plants of the cultivar Wespecarose can also be compared to plants of the *Petunia* cultivar Wespesoro, disclosed in U.S. Plant Pat. No. 14,184. However in side-by-side comparisons conducted in Südlohn-Oeding, Germany, plants of the new *Petunia* and the cultivar Wespesoro differed in the following characteristics:

1. Plants of the new *Petunia* had larger leaves than plants of the cultivar Wespesoro.
2. Plants of the new *Petunia* produced had smaller flower buds than plants of the cultivar Wespesoro.
3. Flowers of the new *Petunia* had larger sepals than flowers of the cultivar Wespesoro.
4. Flowers of the new *Petunia* were smaller than flowers of the cultivar Wespesoro.
5. Flowers of the new *Petunia* were more uniformly pastel pink than flowers of the cultivar Wespesoro.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the colors of the new *Petunia*.

The photograph at the top of the sheet comprises a side perspective view of a typical plant of 'Wespecarose'.

The photograph at the bottom of the sheet comprises a close-up view of a typical flower of 'Wespecarose'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and the following botanical description were grown in 12-cm containers during the spring and summer for about 20 weeks in a glass-covered greenhouse and under conditions that closely approximate commercial production conditions in Südlohn-Oeding, Germany. During the production of the plants, day temperatures were about 20 to 25° C., night temperatures were about 16 to 18° C. and light levels ranged from 3,000 to 50,000 lux.

Botanical classification: *Petunia×hybrida* cultivar Wespecarose.

Parentage:

*Female parent.*—Proprietary *Petunia×hybrida* selection identified as code number 98K6384-340, not patented.

*Male parent.*—Proprietary *Petunia×hybrida* selection identified as code number 98P037, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Numerous, fine, fibrous and well-branched.

Plant description:

*Form.*—Annual flowering plant; upright and outwardly spreading. plant habit Plants roughly spherical in shape. Viscid, glandular pubescent. Freely and continuous basal branching with lateral branches potentially forming at every node.

*Usage.*—Appropriate for hanging baskets, window boxes and patio containers.

*Plant height* (*from soil level to top of plant plane*).—About 15 cm.

*Plant diameter.*—About 70 to 80 cm.

*Stem description.*—Main branches, length: About 80 cm. Main branches, diameter: About 4.4 mm. Lateral branches, length: About 52 cm. Lateral branches, diameter: About 2.1 mm. Internode length: About 3.1 cm. Texture: Densely pubescent. Color: 146A.

*Foliage description.*—Arrangement: Alternate; simple. Length: About 5 cm. Width: About 2.6 cm. Shape: Ovate. Apex: Acute to slightly rounded. Base: Attenuate. Margin: Entire. Aspect: Flat. Texture, upper and lower surfaces: Smooth, leathery, slightly pubescent. Venation pattern: Pinnate. Color: Developing foliage, upper surface: 147A. Developing foliage, lower surface: 147B. Fully expanded foliage, upper surface: 137A. Fully expanded foliage, lower surface: 147B. Venation, upper surface: 146C. Venation, lower surface: 146C and 146D. Petiole length: About 8 mm. Petiole diameter: About 2 mm. Petiole color: 146C and 146D.

Flower description:

*Flower type and habit.*—Single salverform flowers; flowers face upward and outward; single, axillary. Freely flowering habit.

*Natural flowering season.*—Long-day responsive; flowering from April until frost in the autumn in Germany; flowering continuous during this period.

*Fragrance.*—None detected.

*Flower longevity on plant.*—About one week.

*Flower size.*—Diameter: About 5.1 cm. Depth (height): About 3.6 cm. Tube length: About 3.1 cm. Throat diameter, distal end: About 1.3 cm. Tube diameter, proximal end: About 3.3 mm.

*Flower buds.*—Length: About 3.4 cm. Diameter: About 5 mm. Shape: Oblong. Color, towards apex: N80B and N80D. Color, midsection: 144D; venation 144A. Color, base: 144D.

*Petals.*—Arrangement/appearance: Single whorls of five petals, fused into a flared trumpet. Length from throat: About 2.3 cm. Width: About 2.7 cm. Shape: Obtuse. Apex: Obtuse. Margin: Entire. Texture, upper and lower surfaces: Smooth, dull. Color: When opening, upper surface: 75A; towards the throat, 73A. When opening, lower surface: 76C. Fully opened, upper surface: 75B to 75C; towards the throat, 73A. Fully opened, lower surface: 76C to 76D. Flower throat (inside): 74A. Flower tube (outside): 11D. Venation, upper surface: 72A. Venation, lower surface: 144B. Venation, throat: 83A to N79A. Venation, tube: 144B.

*Sepals.*—Arrangement/appearance: Single whorl of five sepals, fused at base; star-shaped. Length: About 1.7 cm. Width: About 3 mm. Shape: Linear. Apex: Rounded. Margin: Entire. Texture, upper and lower surfaces: Densely pubescent; dull. Color, upper and lower surfaces: 137A.

*Peduncles.*—Length: About 3.2 cm. Width: About 1 mm. Strength: Wiry, strong. Texture: Pubescent. Color: 146A overlain with 144A.

*Reproductive organs.*—Stamens: Quantity: About five per flower. Anther shape: Four-parted, ovate. Anther length: About 2.4 mm. Anther width: About 2 mm. Anther color: 85D. Pollen amount: Abundant. Pollen color: 85C to 85D. Pistils: Quantity: One per flower. Pistil length: About 2 cm. Stigma shape: Ovate. Stigma color, immature and mature: 139A. Style length: About 1.6 cm. Style color: 145B to 145C. Ovary color: 145A to 145B. Seed/fruit: Seed and fruit production have not been observed.

Disease/pest resistance: Plants of the new *Petunia* have not been noted to be resistant to pathogens or pests common to *Petunia*.

Temperature tolerance: Plants of the new *Petunia* have been observed to be tolerant to temperatures from 2 to 30° C.

It is claimed:

1. A new and distinct cultivar of *Petunia* plant named 'Wespecarose', as illustrated and described.

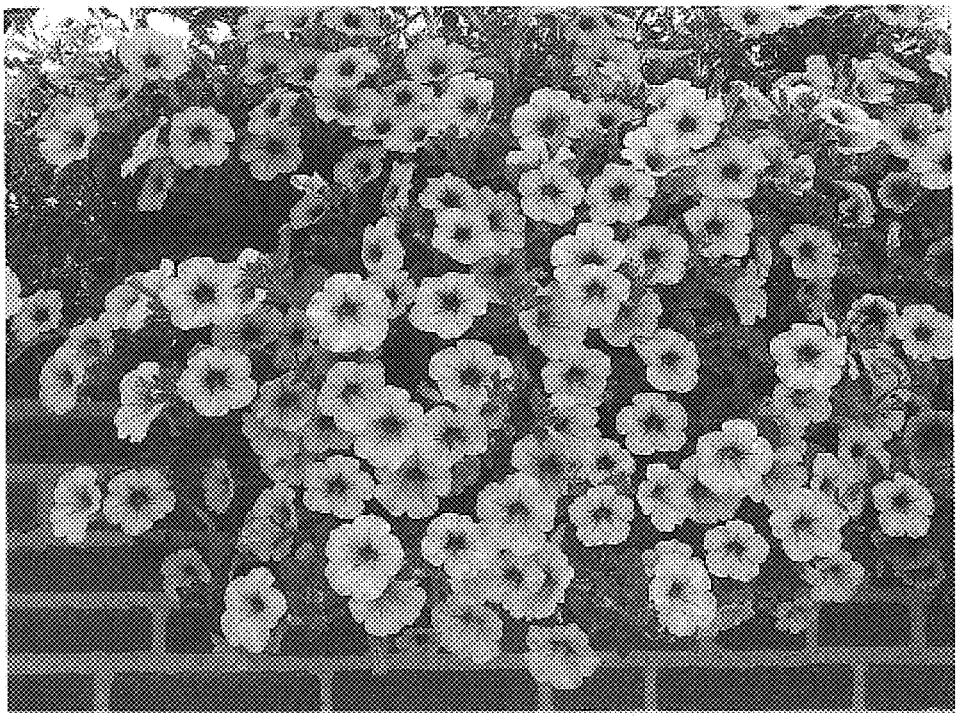
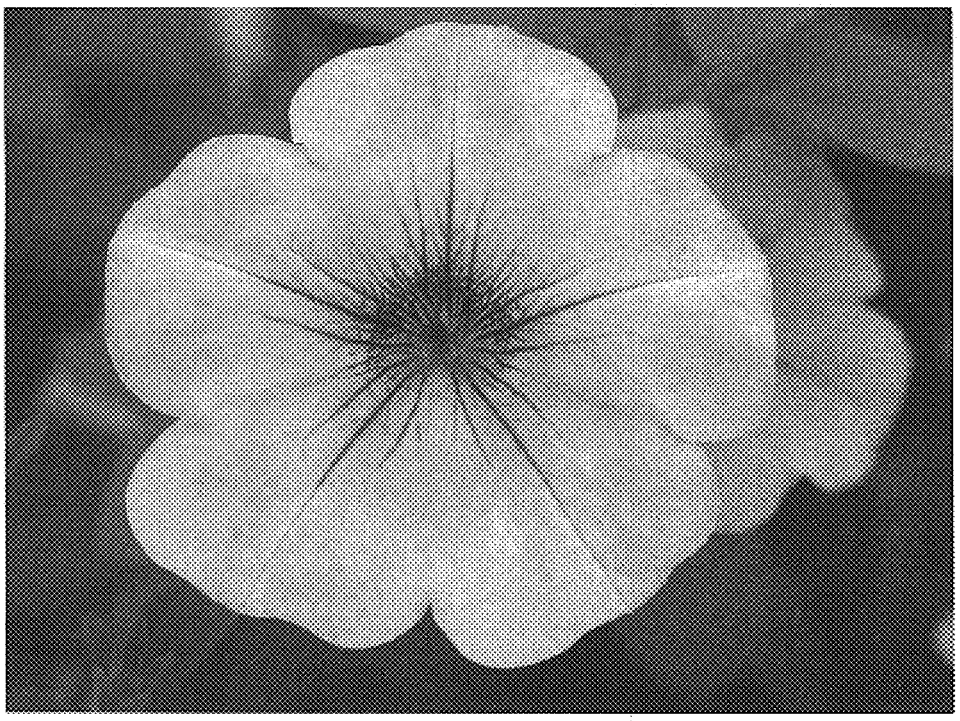

* * * * *